United States Patent [19]
Kline et al.

[11] Patent Number: 5,558,863
[45] Date of Patent: Sep. 24, 1996

[54] METHOD FOR TREATMENT OF HERPES VIRUS INFECTIONS

[75] Inventors: Ellis L. Kline, Pendleton; Walter W. McAlhaney, Anderson, both of S.C.

[73] Assignee: Molecular Rx, Inc., Pendleton, S.C.

[21] Appl. No.: 393,120

[22] Filed: Feb. 21, 1995

Related U.S. Application Data

[63] Continuation of Ser. No. 229,703, Apr. 19, 1994, abandoned, which is a continuation of Ser. No. 860,546, Apr. 3, 1992, abandoned, which is a continuation-in-part of Ser. No. 682,071, Apr. 9, 1991, abandoned.

[51] Int. Cl.$^6$ ..................................... A61K 38/47
[52] U.S. Cl. ......................................... 424/94.61
[58] Field of Search ............................ 424/94.61

[56] References Cited

FOREIGN PATENT DOCUMENTS

4214A1  9/1979  European Pat. Off. .

OTHER PUBLICATIONS

Smiley, L. et al., "Binding of Complement Component C3b to Glycoprotein C is Modulated by Sialic Acid on Herpes Simplex Virus Type 1–Infected Cells," *Journal of Virology*, vol. 55, No. 3, pp. 857–861 (Sep. 1985).
Arora, D. J. S. et al., "In Vitro Enhancement of Human Natural Cell–Mediated Cytoxicity by Purified Influenza Virus Glycoproteins," *Journal of Virology*, vol. 52, No. 3, pp. 839–845 (Dec. 1984).
Yarnell, M. M. et al., "Studies of Tumour Invasion in Organ Culture—II. Effects of Enzyme Treatment," *Europ. J. Cancer*, vol. 5, pp. 265–269 (1969).
Tompkins, W. A. F. et al., "Neuraminidase Reversal of Resistance to Lysis of Herpes Simplex Virus–Infected Cells by Antibody and Complement," *The Journal of Immunology*, vol. 116, No. 2, pp. 489–495 (Feb. 1976).
Varghese, J. N. et al., "Structure of the influenza virus glycoprotein antigeuraminidase at 2.9 Å resolution," *Nature*, vol. 303, pp. 35–40 (May 5, 1983).
Berwick, L. et al., "Some Chemical Factors in Cellular Adhesion and Stickiness," *Cancer Research*, vol. 22, pp. 982–987 (Sep. 1962).
Hatano, H. et al., "Effect of neuraminidase on Fc and C3b receptors on rabbit corneal cells infrects with herpes simplex virus," *Current Eye Research*, vol. 6, No. 1, pp. 53–57 (1987).
Boyd, R. F. et al., "Basic Medical Microbiology," *Basic Medical Microbiology—Second Edition*, p. 527.
Santoli, D. et al., "Mechanisms of Activation of Human Natural Killer Cells Against Tumor and Virus–Infected Cells," *Immunological Review*, vol. 44, pp. 125–163.
Arnheiter, H. et al., "Host Gene Influence on Interferon Action in Adult Mouse Hepatocytes: Specificity for Influenza Virus," *Virology*, vol. 103, 11–20 (1980).
Miller, J. B., "Treatment of Active Herpes Virus Infections with Influenza Virus Vaccine," *Annals of Allergy*, vol. 42, pp. 295–305 (May 1979).

Stein–Streilein, J. et al., "In Vivo Treatment of Mice and Hamsters with Antibodies to Asialo GM1 Increases Morbidity and Mortality to Pulmonary Influenza Infection," *The Journal of Immunology*, vol. 135, No. 4, pp. 1435–1441 (Feb. 15, 1986).
Yasukawa, M. et al., "Autologous Herpes Simplex Virus–Infected Cells are Lysed by Human Natural Killer Cells," *The Journal of Immunology*, vol. 131, No. 4, pp. 2011–2016 (Oct. 1983).
Ching, C. et al., "Natural Killing of Herpes Simplex Virus Type 1–Infected Target Cells: Normal Human Responses and Influence of Antiviral Antibody," *Infection and Immunity*, vol. 26, No. 1, pp. 49–56 (Oct. 1979).
St. Geme, Jr., J. W. et al., "Impaired Cellular Resistance to Herpes–Simplex Virus in Wiskott–Aldrich Syndrome," *The New England Journal of Medicine*, vol. 273, No. 5, pp. 229–234.
Rawls, W. E., "Herpes Simplex Virus Infections: Type 1 and Type 2 Viruses," *Laboratory Diagnosis of Viral Infections—Edited by Edwin H. Lennette*, Chapter 19, pp. 313–340.
"The Epstein–Barr Virus", edited by M. A. Epstein et al., published by Springer–Verlag, pp. 298–320 (1979).
Dajer, T., "Herpes Key," *Discover*, p. 20 (Nov. 1990).
Herring, T. "A Salivary Herpesvirus Interacts with HIV," *ASM News*, vol. 56, No. 10, pp. 522–523 (1990).
Trinchieri, G. et al., "Anti–Viral Activity Induced by Culturing Lymphocytes with Tumor–Derived or Virus–Transformed Cells," *J. Exp. Med.*, pp. 1299–1313.
Djeu, J. Y. et al., "Positive Self Regulation of Cytotoxicity in Human Natural Killer Cells by Production of Interferon upon Exposure to Influenza and Herpes Viruses," *Journal of Experimental Medicine*, vol. 156, pp. 1222–1234 (Oct. 1982).
Nahmias, A. J. et al., "Infection with Herpes–Simplex Viruses 1 and 2," *The New England Journal of Medicine*, vol. 289, No. 13, pp. 667–674 (Sep. 27, 1973).
McTaggart, S. P. et al., "Fc Receptors Inducted by Herpes Simplex Virus—I. Biologic and Biochemical Properties," *The Journal of Immunology*, vol. 121, No. 2, pp. 727–730 (Aug. 1978).
Levy, J. A. et al., "Human Herpevirus 6 Inhibits Human Immunodeficiency Virus Type 1 Replication in Cell Culture," *Journal of Clinical Microbiology*, vol. 28, pp. 2362–2364 (Oct. 1990).
Lennette, E. T., "Diagnosis of Epstein–Barr Virus Infections," Chapter 16, pp. 257–271.
Welsh, R. M., "Natural Cell–Mediated Immunity During Viral Infections," *Natural Resistance to Tumors and Viruses*, edited by O. Haller, published by Springer–Verlag, pp. 83–106.

(List continued on next page.)

*Primary Examiner*—Michael G. Wityshyn
*Assistant Examiner*—Jean C. Witz
*Attorney, Agent, or Firm*—Jones & Askew

[57] ABSTRACT

A method and composition are provided for treatment of herpes virus infections. The invention comprises the administration of a low level of neuraminidase protein or a derivative thereof.

7 Claims, No Drawings

OTHER PUBLICATIONS

Haller, O., "Inborn Resistance of Mice to Orthomyxoviruses," *Current Topics in Microbiology and Immunology*, edited by W. Henle, pp. 25–52.

Strauss, S. E. et al., "Acyclovir treatment of the chronic fatigue syndrome: Lack of efficacy in a placebo–controlled trial," *N. Engl. J. Med.*, Abstract: 319 (26), pp. 1692–1698 (1988) Abstract.

Lung, M. L. et al., "Detection of Distinct Epstein–Barr Virus Genotypes in NPC Biopsies from Southern Chinese and Caucasians," *Int. J. Cancer*, vol. 52 (1), pp. 34–37 (1992) Abstract.

Levine, P. H. et al., "Clinical Epidemiologic and Virologic Studies in Four Clusters of the Chronic Fatigue Syndrome," *Arch Intern Med.*, vol. 152 (8), pp. 1611–1616, (1992) Abstract.

METHOD FOR TREATMENT OF HERPES VIRUS INFECTIONS

CROSS REFERENCE TO RELATED APPLICATION

This is a continuation of application Ser. No. 08/229,703, filed Apr. 19, 1994, now abandoned, which is a continuation of application Ser. No. 07/860,546 filed on Apr. 3, 1992, now abandoned, which is a continuation-in-part of U.S. patent application Ser. No. 07/682,071 filed on Apr. 9, 1991, now abandoned.

FIELD OF THE INVENTION

The present invention is related to a method and composition for the treatment of herpes related disorders. More particularly, the present invention relates to the treatment of a herpes related disorder comprising the step of administration of neuraminidase or a compound related to neuraminidase at very low concentrations to a human or animal with the herpes related disorder.

BACKGROUND OF THE INVENTION

As used herein, the term "neuraminidase" means any protein that has neuraminidase activity or has an amino acid sequence that is similar to a protein which has neuraminidase activity. The neuraminidase that can be used to practice the present invention can also be inactivated enzyme or part of the enzyme. The term "herpes related disorder" means any disorder that is effected or mediated by a herpes virus infection. The term "herpes virus" means any virus in the herpes family. These include, but are not limited to, herpes simplex types 1 and 2, Epstein-Barr viruses, varicellazoster, cytomegaloviruses, *Herpesvirus simiae* and human herpesvirus-6.

Herpes Virus Infections

More than 50 herpes viruses are known to infect over 30 different species. A. J. Nahmias and B. Roizman, *New Engl. J. Med.* 289, pp. 667–674 (1973). The most clinically significant of these are the two naturally occurring variants of herpes simplex virus (HSV). Man is the sole reservoir of this virus. The herpes simplex virus was first isolated in 1920. B. Lipschutz, *Arch. Derm. Syph.* (Berl) 136, pp. 428–482 (1921). In 1961, two serotypes were differentiated. Generally, HSV-1 infects non-genital sites while HSV-2 infects genital sites. It is possible, however, to isolate HSV-1 in a genital herpes case. Transmission is direct. Localized ulcers or lesions in the oral cavity, eye, skin or reproductive tract usually develop after infection. Dissemination can cause encephalitis in neonates and the immunosuppressed. The virus can remain latent, presumably for years, until a relapse is triggered by stress, environmental factors, other medications, food additives or food substances (see A. J. Nahmias and B. Roizman, *New Engl. J. Med.* 13, pp. 667–674 (1973); W. E. Rawls, E. H. Lennette (eds.), *Laboratory Diagnosis of Viral Infections*, Marcel Dekker, Inc., New York, pp. 313–328 (1985)).

Another pathogen from the herpes virus group is the Epstein-Barr virus. Discovered in the 1960's, it is the principal etiologic agent of infectious mononucleosis and has been associated with Burkitt's lymphoma and nasopharyngeal carcinoma malignancies (see W. Henle and G. Henle, M. A. Epstein and B. G. Achong (eds.), THE EPSTEIN-BARR VIRUS, Springer-Verlag, Berlin, p. 297 (1979)). Infectious mononucleosis is characterized by lymphadenopathy, fever and pharyngitis. As with the HSV variants, the Epstein-Barr virus may establish a latent infection which may be reactivated when the host is immunosuppressed (see E. T. Lennette, E. H. Lennette (eds.), LABORATORY DIAGNOSIS OF VIRAL INFECTIONS, Marcel Dekker, Inc., New York, pp. 257–271 (1985)).

Also a herpes virus, the varicellazoster (VZ) virus is the causative agent of both varicella (chicken pox) and zoster (shingles). Varicella occurs primarily in childhood, whereas the more localized zoster occurs in the elderly and immunocompromised. Zoster is, in fact, due to a reactivation of a latent VZ infection. Patients suffer painful, vesicular skin lesions (see A. Gershon, E. H. Lennette (eds.), LABORATORY DIAGNOSIS OF VIRAL INFECTIONS, Marcel Dekker, Inc., New York, pp. 329–340 (1985)). Currently, analgesics provide the only treatment for shingles (see R. Boyd, et at., BASIC MEDICAL MICROBIOLOGY, 2nd Edition, Little, Brown and Company, Boston, p. 527, (1981)).

It has been reported that patients with severe herpes simplex (HSV) infections had no antibody titers above that observed in normal patients. This absence of immune response was speculated to be due to a deficiency in the patient's cell mediated immune response (see J. W. St. Geme, et al., *New Engl. J. Med.* 273, pp. 229–234 (1965)). While there is antibody to HSV-1 in most normal adults, the humoral immune response (antibody production) to the virus appears not to be sufficient to fight off the disease (see C. Ching and C. Lopez, *Infect. Immun.* 26, pp. 49–56 (1979)). The presence of an immunologically recognized glycoprotein on the cell membrane of herpes infected cells (glycoprotein C) has also been observed. This glycoprotein C is thought to function as a receptor for the third component of immune complement (see M. L. Smiley and H. M. Friedman, *J. Vir.* 55, pp. 857–861 (1984)).

The absence of a pronounced immune response indicates that other necessary factors are not present or effective in herpes virus infections. In vitro studies have shown that HSV-1 and HSV-2 infected cells can be lysed by the cell-mediated immune NK cells when present in significant numbers (see C. Ching and C. Lopez, *Infect. Immun.* 26, pp. 49–56 (1979); M. Yasukawa and M. J. Zarling, *J. Immunol.* 131, pp. 2011–2016 (1983)). Many patients with severe herpes simplex infections have very low NK cell response (see M. Yasukawa and M. J. Zarling, *J. Immunol.* 131, pp. 2011–2016 (1983)).

Unlike the herpes virus, the influenza virus has been shown experimentally to stimulate NK cells in vitro. It has been suggested that one of the two neuraminidase glycoproteins may be responsible for this stimulation (see J. Arora, et al., *J. Virol.* 52, pp. 839–845 (1984)). To further define the involvement of NK cell-mediated immune response, the morbidity and mortality effect by influenza viral infections in mice and hamsters in the presence of anti-NK antibodies was investigated (see J. Stein-Stereilen and J. Guffee, *J. Immunol.* 136, pp. 1435–1441 (1986)). The dramatic increase in morbidity and mortality suggested that both the neuraminidase, as well as NK cells, are necessary for this anti-influenza viral immune response.

This anti-NK induced effect with influenza infection is similar to that observed when HSV infections are severe (see M. Yasukawa and M. J. Zarling, *J. Immunol.* 131, pp. 2011–2016 (1983)). Another immunomodulator, interferon, was also shown to increase several fold with influenza virus administered intranasally to patients (see F. A. Ennis, et al., Lancet, p. 891–893 (1981)). The proportional relationship between NK cells and interferon has been well established (see G. Trinchieri, et al., *J. Exp. Med.* 147, pp. 1299–1313

(1978); D. Santoli and H. Koprowski, *Immunol Rev.* 44 p. 125–163 (1979); T. Timonen, et al, *Eur. J. Immunol.* 10, pp. 422–427 (1980); O. Hailer, *Curr. Top. Microbiol. Immunol.* 92, pp. 25–52 (1981); T. Timonen, J. R. Otaldo, and R. B. Herberman, *J. Exp. Med.* 153, pp. 569–582 (1981); R. M. Welsh, *Curr. Top. Microbiol. Immunol.* 92, pp. 83–106 (1981); J. Djeu, et al., *J. Exp. Med.* 156, pp. 1222–1234 (1982)). The influenza virus has neuraminidase glycoproteins as well as hemagglutinin, all of which are thought to play a major role in NK cell-mediated activity (see, D. Arora, et al., *J. Virology* 52, pp. 839–845 (1984)).

Thus, the apparent persistence of the HSV infection is associated with the absence of the body's immune response to be triggered in herpes infected patients (see J. W. St. Geme, et al., New Engl. *J. Med.* 273, pp.229–234 (1965); A. J. Nahmias and B. Roizman, *New Engl. J. Med.* 289, pp. 667–674 (1973); C. Ching and C. Lopez, *Infect. Immun.* 26, pp. 49–56 (1979); J. Stein-Stereilen and J. Guffee, *J. Immunol.* 136, pp. 1435–1441 (1986); M. Yasukawa and M. J. Zarling, *J. Immunol.* 131, pp. 2011–2016 (1983)). The absence of natural killer cell cell-mediated immune response in these patients has been speculated as one possible reason for the persistence of the disease state (see M. Yasukawa and M. J. Zarling, *J. Immunol.* 131, pp. 2011–2016 (1983); C. Ching and C. Lopez, *Infect. Immun.* 26, pp. 49–56 (1979); Stein-Stereilen and J. Guffee, *J. Immunol.* 136, pp. 1435–1441 (1986)).

Disorders Related to Herpes Infection

A number of disorders are thought to be related to herpes virus infection. For example, HIV infection in vitro has been reported to be enhanced in the presence of human herpes virus-6 (HHV-6) (see Gallo, et al., ASM News 56, p. 523 (1990)). Levy, et at., reported that the HHV-6 inhibited infection of peripheral blood mononuclear cells and purified $CD4^+$ lymphocytes (see Levy, et al., *J Clin. Micro.* 28, pp. 2362–2364 (1990)).

Nasopharyngeal carcinoma has been associated with Epstein-Barr viral antigens. Patients with nasopharyngeal carcinoma have been shown to exhibit antibodies to soluble Epstein-Barr virus antigens. In addition, antibody titers in patients suffering from nasopharyngeal carcinoma appear when tumor growth is progressive and the same antibodies are frequently not detectable when tumors are regressing (see Piessens, W. F., Cancer, (Phila) 26, p. 1214 (1970)).

Herpes viruses have also been implicated in chronic fatigue syndrome. In particular, the Epstein-Barr virus has been associated with the disease, based in part on several studies describing patients with atypical profiles of antibodies to the Epstein-Barr virus. (For a review, see Lopez, C., (ed.) *Immunology and Pathogenesis of Persistent Virus Infections*, American Society for Microbiology, Washington, D.C., p. 286 (1988)). Other diseases in which the Herpes virus is implicated are shingles, Herpes Type I (fever blisters), Herpes Type 2 (genital herpes), Burkitt's lymphoma, and mononucleosis (see Davis, et al., MICROBIOLOGY, 4th ed., J. B. Lippincott Company, Philadelphia, p. 929 (1990)).

As summarized hereinabove, infections by herpes-related viruses have been implicated in a wide range of diseases. What is needed is a method of treating disorders that are associated with herpes virus infections so that the immune system of the human or animal can effectively correct the symptoms of the disease state, presumably allowing the immune system to target the diseased tissue. The method and composition should be safe and easy to administer and should be effective in a short period of time after administration with negligible, if any, side effects over a period of time.

Summary of the Invention

The present invention provides a method and composition for alleviating the symptoms of disease states associated with herpes virus and related disorders. The present invention comprises administration to the human or animal with the herpes related disorder of an effective dose of neuraminidase or a fraction or derivative thereof. The effective dose is extremely low and does not cause side effects such as an immune response to the neuraminidase protein.

It has been found that the administration of extremely low amounts of neuraminidase to a human or animal which has been infected with a herpes-type virus causes the elimination of the symptoms of the herpes-mediated disorder, presumably through modulation of the immune function.

In practice, the present invention comprises the administration of less than approximately $10^{-2}$ mg per dosage unit to a human or animal that has been infected with a herpes-type virus. A preferred dose of neuraminidase or active derivative thereof is between approximately $10^{-2}$ mg to $10^{-8}$ mg. A more preferred dose of neuraminidase is between approximately $10^{-3}$ mg and $10^{-7}$ mg. The most preferred dose of neuraminidase is approximately $10^{-4}$ mg. Preferably, the total periodic daily dosage does not exceed about $10^{-2}$ mg per subject, and still more preferably does not exceed from about $5\times10^{-3}$ to $10^{-4}$ mg.

In a second aspect of the invention there is provided a pharmaceutical composition comprising a vehicle for a single administration of neuraminidase or fraction or derivative thereof which comprises an amount of up to about $10^{-2}$ mg neuraminidase or fraction or derivative thereof and pharmaceutically inert ingredients. In a preferred aspect the pharmaceutical composition has an amount of between approximately $10^{-2}$ to about $10^{-8}$ mg neuraminidase or fraction or derivative thereof.

In practice, the present invention comprises the partitional administration of an amount not to exceed approximately $10^{-2}$ mg, although, in certain cases, the total amount of neuraminidase administered in any one day may exceed the preferred limit. The neuraminidase can be administered as a liquid or it can be administered as a solid wherein the neuraminidase is embedded or admixed in a biodegradable or bioerodable matrix. The matrix can be a time release matrix. These matrices are well known to those of ordinary skill in the art and are not critical to the present invention. The neuraminidase can be administered by injection or by sublingual route. In one embodiment, the vehicle is an aqueous solution that is contained within an inert container. In another variation, the composition is in the form of a suppository. The liquid form of the composition can be injected subcutaneously, intramuscularly or intravenously. In addition, the composition can be administered through the muscosal membranes such as nasal membranes.

Accordingly, it is an object of the present invention to provide a method for treating diseases that are associated with herpes-type virus infections.

It is yet another object of the present invention to provide a method and composition for the treatment of chronic fatigue syndrome.

It is yet another object of the present invention to provide a method and composition for the treatment of cold sores.

It is yet another object of the present invention to provide a method and composition for the treatment of nasopharyngeal carcinoma.

It is yet another object of the present invention to provide a method and composition for the treatment of HIV infection.

It is yet another object of the present invention to provide a method and composition for the treatment of shingles.

It is yet another object of the present invention to provide a method and composition for the treatment of Burkitt's lymphoma.

It is yet another object of the present invention to provide a method and composition for the treatment of fever blisters.

It is yet another object of the present invention to provide a method and composition for the treatment of mononucleosis.

These and other objects, features, and advantages will become apparent after a review of the following detailed description of the disclosed embodiments and the appended claims.

DETAILED DESCRIPTION

The present invention provides a method and composition for alleviating the symptoms of disease states associated with herpes virus and related disorders. The present invention comprises administration to the human or animal with the herpes related disorder of an effective dose of neuraminidase or a fraction or derivative thereof. The effective dose is extremely low and does not cause an immune response to the neuraminidase-type protein.

In accordance with the invention, there is provided a novel method for stimulating the appropriate metabolic and cellular regulatory systems (immune, CNS, endocrine or cellular physiological events), which retard the progress of the symptoms of HSV-1 and HSV-2 and related disease states. The present invention presumably results in triggering control processes that correct the body's immune response such that it can properly target the herpes infected tissue, and/or reversing the viral expression in the infected cells through secondary cell control metabolites.

The alleviation of herpes symptoms observed following parenterally administered neuraminidase, as described herein, reflects stimulation of appropriate metabolic regulatory systems in the herpes infected patients such that viral expression, immune dysfunction and/or synthesis of controlling metabolites reverse the symptoms of the herpes infection. This reprogramming to establish proper homeostasis results in clinical improvement of treated herpes patients.

When a cellular parasite (such as a virus) initially infects a cell in the body, unique antigens are derived which are displayed on the infected cell surface (see A. Nahmias and B. Roizman, *New Eng. J. Med.* 289, pp. 667–674 (1973)). These novel antigens, in turn, during the first exposure to the body, are recognized by receptors on various circulating T cell lymphocytes. This cell-mediated response provides for one of the major components in the body's defenses against infectious agents (immune response). Cells which are involved in this immune response are cytotoxic T cells or natural killer cells (NK). These cells lyse the infected cells or helper T cells (HT). The HT cells apparently assist in T-cell mediated antibody-antigen interactions. Another T cell, the suppressor T cell, which is also important in immune responses, can suppress the reaction of B cell mediated antibody-antigen interaction or HT and NK immune response.

Transport of many viruses and bacteria through cell mucin on the cell surface into the cell appears to be facilitated by the reaction of neuraminidase on its cell surface. The reaction by neuraminidase on the cell surface cleaves the sialic acid component, which also destroys a hemagglutinin receptor site on the host cell (see J. N. Varghese, W. G. Laver, and P. M. Colman, *Nature* (London) 303, pp. 35–40 (1983)). When the sialic acid component is present on the cell surface, it can stabilize certain cells through an increase in cellular adhesiveness (see L. Berwick and D. R. Coman, *Cancer Res.* 22, pp. 982–986) or other cells through facilitation of cellular mobilization (see M. M. Yarnell and E. J. Ambrose, Eura. *J. Cancer* 5, pp. 265–269 (1969)).

The neuraminidase (Acyl-neuraminyl hydrolase: EC3.2.1.18) that can be used in practicing the present invention can be from any source including, but not limited to, *Arthrobacter ureafaciens, Vibrio cholerae, Clostridium perfringens*, or from mammalian sources.

Typically, a pharmaceutical dosage unit of the present invention for the delivery of neuraminidase in a low concentration comprises a liquid or solid pharmaceutically acceptable carder and an effective amount of neuraminidase. The aforesaid effective amount is preferably from between approximately $10^{-2}$ to about $10^{-8}$ mg, and still more preferably about $10^{-4}$ mg neuraminidase in the dosage unit in association with pharmaceutically acceptable excipients. The preferred carrier is 0.1% phenol in 0.9% sodium chloride (USP).

It should be noted here that although there have been reports of treating other viral infections such as rhinovirus and influenza infections with neuraminidase type proteins, these reports used extremely high doses of neuraminidase. For example, European Patent No. 0 004 214 discloses the administration of between 300 U and 5000 U of neuraminidase for the treatment of the aforementioned viruses. This is equivalent to approximately 15 mg to 250 mg of neuraminidase per dose. In the present invention, the dose range of neuraminidase is between 0.0001 mg to 0.01 mg. Thus, the minimum dose disclosed in the '214 patent is 150,000 times the minimum dose that is effective in the present invention and is 1,500 times more than the maximum dose according to the present invention. Administration of neuraminidase at the high concentrations taught by the '214 patent may result in a wide variety of side effects including allergic reactions, cross-reactivity with cell surface proteins, and the potential for anaphylactic reactions with subsequent administration of the protein. At the concentrations taught by the '214 patent, the therapeutic effects of the method are not observed for any herpes-related disorder.

The neuraminidase can be administered through standard methods, including intravenous, intramuscular, and subcutaneous routes. The neuraminidase can also be administered by sublingual and intranasal routes. Because the effective amount of neuraminidase in a dose is so low, the composition according to the present invention can also be administered transdermally, anally or orally. The dosage units can be either liquid or solid. Typically, the dosage unit may be administered up to a maximum of about 15 times per day.

In contrast to experiments cited earlier, the novel low dose application is preferably not administered directly to infected cells at lesion sites, but is preferably administered systemically, so as to elicit the body's own defense systems to reverse the disease state. It is believed that the systemic administration of the low dose neuraminidase is not acting directly on the herpes infected cells. When neuraminidase is applied directly to tissue culture, where its action is on the HSV infected cells, it is at a much higher concentration of neuraminidase than is used in the present invention. For example, neuraminidase used in the cell culture research is as high as 0.03 mg of neuraminidase protein /1,000–10,000 rabbit corneal cells when employed to discover the extent to which immune complement functions (see H. Hatano and J. O. Oh, *Current Eye Res.* 6, pp. 53–57 (1987)), and 3 mg neuraminidase protein /100,000 cultured human cells when applied to discover lysis enhancement (see W. A. F. Tompkins, et al., *J. Immunol.* 116, pp. 489–495 (1976)). This 0.03 µg concentration per cell in the in vitro studies is approximately, ten thousand billion fold higher concentration of neuraminidase than the therapeutic dose used per body cell of the instant invention.

Although not wanting to be bound by the following explanation, it is believed for the mechanism of this invention is that the small amount of this protein administered is sufficient to trigger a negative feedback mechanism to the body such that the body's immune system or various metabolites can effectively suppress or target the infected cells. Under this theory, the low level of neuraminidase, or a derivative thereof, gives a signal to the body to correct the abnormal synthesis/degradation process. The body's sensors are then adjusted to produce the necessary immune components or messenger metabolites to allow proper recognition of the herpes infected or expressing cells, alleviating the abnormal processing. The immune system, as well as the endocrine and CNS control systems, probably play an integral regulatory role in response to the low dose therapy, with the neuraminidase functioning through mechanisms that reverse the herpes disease symptoms.

The invention is further illustrated by the following examples, which are not to be construed in any way as imposing limitations upon the scope thereof. On the contrary, it is to be clearly understood that resort may be had to various other embodiments, modifications and equivalents thereof which, after reading the description herein, may suggest themselves to those skilled in the art without departing from the spirit of the present invention and/or the scope of the appended claims.

Example I

A 40 year old female subject was treated with the therapeutic agent for oral herpes infection. The patient received a sublingual dose of $10^{-4}$ mg neuraminidase (Sigma Chemical Company, St. Louis, Mo.) in a 50 microliter dosage of 0.1% phenol in 0.9% NaCl at fifteen minute intervals for two and one half hours, by which time the lesion pain fully disappeared. The following morning, lesion pain returned so the treatment is reinitiated. After a two hour treatment period, the lesion pain again disappeared. The herpes lesions healed within a few days and did not reoccur as frequently (monthly) as they had during the previous twenty years.

Example II

A 37 year old male subject had shingles with severe associated pain for about one month prior to initiation of treatment with the therapeutic agent. The pain subsided dramatically after twelve hourly sublingual 50 microliter dosings of $10^{-4}$ mg neuraminidase in 0.1% phenol in 0.9% NaCl. The patient was pain-free for three days following the first treatment phase. Slight pain was experienced on the fourth day at which time he started sublingual administration every fifteen minutes for two hours. After this treatment, pain subsided. He was placed on a maintenance treatment regime of one dose per day for three weeks. He has remained completely free of shingles associated symptoms during the seventeen months of follow-up observation.

Example III

A 33 year old patient had a 10 year history of oral herpes with a reoccurrence rate of several episodes a month. Lesions were severe and would often make the patient nauseated from the severity of the outbreak. According to past history, if the patient took nothing for the outbreak of lesions, the infectious (feverish, throbbing) period would normally last three to five days, then it would be two weeks before the condition was completely healed.

Since initiating therapy with the therapeutic agent, when the patient first noticed the lesions, she would begin taking the dosage unit of $10^{-4}$ mg neuraminidase per 50 microliters of 0.9% NaCl with 0.1% NaCl every fifteen minutes for one hour thereafter, until the burning sensation disappeared. If the lesions were discovered in the very early stages, i.e., when an itching sensation developed, before the lesions were readily apparent, the lesion would never fully develop and the progression would be halted before the full blisters developed.

The patient reported that this had not been possible with other medications taken for her oral herpes. If the patient did not apply the treatment early enough or if the lesions developed overnight while the patient slept, the blisters would be painful, making her nauseous. Within a few sublingual administrations of the dosage, relief would be experienced in the form of a decrease in the infection and pain level, as well as an elimination of the nausea resulting therefrom. Subsequently, the frequency of outbreaks has also decreased dramatically.

Example IV

A 21 year old female, diagnosed with genital herpes, had a three year history of frequent HSV-2 infections. After initiation of sublingual treatment with $10^{-4}$ mg therapeutic agent per 50 microliters, four times per day following the first signs of discomfort, the HSV symptoms were blocked and reversed without further progression to the full blown disease state. Prophylactic treatment was continued for two days after the HSV symptoms were no longer evident. The patient has remained herpes symptom-free to date (one year).

Example V

A 40 year old female, with a large, painful lesion under the tongue, was treated with $10^{-4}$ mg of the therapeutic agent per 200 microliters, administered by subcutaneous injections. The pain was dramatically reduced within six hours of treatment initiation and had completely disappeared by the next morning. Prophylactic subcutaneous treatments were continued for another three days. The lesion was fully healed within five days of initial treatment.

Example VI

Three patients, ages 45, 53 and 67, were treated for chronic fatigue syndrome, a disease associated with the Epstein-Barr virus. Neuraminidase was administered at a dose of $10^{-4}$ mg sublingually 3 times a day for 3 days. All three patients showed marked improvement with this regimen.

Example VII

A patient with nasopharyngeal carcinoma which is associated with Epstein-Barr virus, underwent surgery with subsequent radiation and chemotherapy. The treatments failed to halt the spread and growth of the tumor. Administration of neuraminidase (4 doses daily) was begun followed one week later by cyclophosphamide therapy. After 3 weeks of neuraminidase treatment, there were indications that symptoms of severe peripheral neuropathy, brought about by the chemotherapy, were being reversed.

It should be understood, of course, that the foregoing relates only to a preferred embodiment of the present invention and that numerous modifications or alterations may be made therein without departing from the spirit and scope of the invention as set forth in the appended claims.

We claim:

1. A method for treating herpes virus infections selected from the group consisting of HSV1, HSV2 and varicella-zoster in a human or animal comprising the step of administering to the human or animal with the herpes virus infection a solution of neuraminidase at a dose of from between about $10^{-2}$ mg to about $10^{-8}$ mg.

2. The method of claim 1, wherein the solution of neuraminidase is administered periodically.

3. The method of claim 1, wherein the dose of neuraminidase is between approximately $10^{-3}$ mg and $10^{-7}$ mg.

4. The method of claim 1, wherein the dose of neuraminidase is approximately $10^{-4}$ mg.

5. The method of claim 1, wherein neuraminidase is administered by subcutaneous injection.

6. The method of claim 1, wherein the neuraminidase is administered with a pharmaceutically acceptable carrier.

7. The method of claim 6, wherein the pharmaceutically acceptable carrier comprises 0.1% phenol in 0.9% sodium chloride.

* * * * *